(12) United States Patent
Jeschke et al.

(10) Patent No.: US 6,730,314 B2
(45) Date of Patent: May 4, 2004

(54) CULTURING ENCAPSULATED CHONDROCYTES UNDER REDUCED OXYGEN PARTIAL PRESSURE TO PRODUCE CARTILAGE IMPLANTS

(75) Inventors: Brigitte Jeschke, Kelkheim (DE); Jörg Meyer, Heusenstamm (DE); Peter Adamietz, Hamburg (DE); Norbert Meenen, Hamburg (DE); Christiane Göpfert, Hamburg (DE)

(73) Assignee: Merck Patent Gesellschaft, Darmstadt (DE)

( * ) Notice: Subject to any disclaimer, the term of this patent is extended or adjusted under 35 U.S.C. 154(b) by 128 days.

(21) Appl. No.: 09/940,854

(22) Filed: Aug. 29, 2001

(65) Prior Publication Data

US 2002/0052044 A1 May 2, 2002

(30) Foreign Application Priority Data

Aug. 29, 2000 (DE) .......................... 100 42 484

(51) Int. Cl.$^7$ ........................... A61F 2/00; C12N 11/10; C12N 5/06; C12N 5/08
(52) U.S. Cl. ...................... 424/423; 424/93.7; 435/178; 435/382; 435/395; 435/404
(58) Field of Search ................................ 435/325, 178, 435/382, 395, 404; 424/93.7, 422, 423

(56) References Cited

PUBLICATIONS

Minas, et al., "Current Concepts in the Treatment of Articular Cartilage Defects," Orthopedics, vol. 20, No. 6, Jun. 1997, pp. 525–538.

Bonaventure et al., "Reexpression of Cartilage–Specific Genes by Dedifferentiated Human Articular Chondrocytes Cultured in Alginate Beads," Experimental Cell Research, 212 (1994), pp. 97–104.

Yaeger et al., "Synergistic Action of Transforming Growth Factor–β and Insulin–like Growth Factor–I Induces Expression of type II Collagen and Aggrecan Genes in Adult Human Articular Chondrocytes," Experimental Cell Research, 237 (1997), pp. 318–325.

*Primary Examiner*—David M. Naff
(74) *Attorney, Agent, or Firm*—Millen, White, Zelano & Branigan

(57) ABSTRACT

A process is provided for the production of a human cartilage implant from chondrocytes cultured in vitro, which come as close as possible to the original with respect to their biochemical composition and biomechanical properties. Up to 20% vol. of human serum is used as medium addition in the process. The chondrocytes can be kept in monolayer culture until the 12$^{th}$ passage in order firstly to be re-differentiated, incubated under a reduced oxygen partial pressure, and subsequently stimulated to form a three-dimensional cartilage tissue due to aggregation under an oxygen partial pressure of 21%. In an embodiment, chondrocytes in alginate beads are cultured in a nutrient solution, which may contain human serum and one or more chondrogenic growth factors, under an oxygen partial pressure of less than 20 volume %, isolated from the alginate beads by a treatment with a chelating agent, aggregated by centrifugation and cultured under an oxygen partial pressure of: –21 volume %.

24 Claims, 1 Drawing Sheet

CULTURING ENCAPSULATED CHONDROCYTES UNDER REDUCED OXYGEN PARTIAL PRESSURE TO PRODUCE CARTILAGE IMPLANTS

The invention relates to a process for the production of human cartilage implants from, e.g., chondrocytes cultivated in vitro.

BACKGROUND OF THE INVENTION

Articular cartilage suffers from a very limited ability for repair of joint surface damage. A workable concept for surgical therapy of joint surface damage based on cartilage produced in vitro has the prerequisite, inter alia, that cartilage implants can be obtained from autologous cells (chondrocytes or mesenchymal stem cells), which come as close as possible to the original with respect to their biochemical composition and biomechanical properties. In principle, both chondrocytes and mesenchymal stem cells are suitable for this purpose.

Since autologous cells are only available in small number in the form of a biopsy, there is a necessity for effective in vitro expansion. This is a particular challenge, since, as is known from the literature, a loss of the differentiated phenotype which increases with the number of passages is observed. This means that while the synthesis of cartilage can be promoted merely by increasing cell/cell contact on use of primary cells or of first-passage cells, this method fails if cells have to be passaged more frequently for the purposes of multiplication. Neither has it hitherto been achieved in human cells to halt the decrease in the chondrogenesis potential during the multiplication phase by means of various additives, such as certain sera or certain growth factors, such as bFGF.

It is already known to multiply human cartilage cells in a cell culture vessel, e.g., a dish/bottle, (cells de-differentiate in this monolayer cultivation) with subsequent re-differentiation of the cells in alginate gel. The cells and their surrounding matrix are subsequently analyzed using different methods within the alginate or after dissolution of the cells out of the alginate (Bonaventure J. et al., Exp. Cell Res. 212 (1):97–104 (1994), Reexpression of Cartilage-Specific Genes by Dedifferentiated Human Articular Chondrocytes Cultures in Alginate; Yaeger P. C. et al. Exp. Cell Res. 237:318–325 (1997), Synergistic Action of Transforming Growth Factor-$\beta$ and Insulin-like Growth Factor-I Induces Expression of Type II Collagen and Aggrecan Genes in Adult Human Articular Chondrocytes).

SUMMARY OF THE INVENTION

An object of the present invention is to provide a process for the cultivation of a substantially differentiated cartilage tissue (not individual cells) of sufficient size (e.g., having a diameter or side dimensions of about 0.1–5 cm, preferably about 0.2 to 3 cm) which avoids the above-mentioned disadvantages from the prior art, so that the cartilage tissue can be implanted in a "press-fit" manner (i.e. with rotationally stable seating) in joint cartilage defects.

Upon further study of the specification and appended claims, further objects and advantages of this invention will become apparent to those skilled in the art.

BRIEF DESCRIPTION OF THE DRAWINGS

Various other features and attendant advantages of the present invention will be more fully appreciated as to same becomes better understood when considered in conjunction with the accompanying drawing, FIG. 1. which shows an immunoblot demonstrating the effect of reduced oxygen pressure on the collagen type II/collagen Type I ratio.

DETAILED DESCRIPTION OF THE INVENTION

Figure 1:
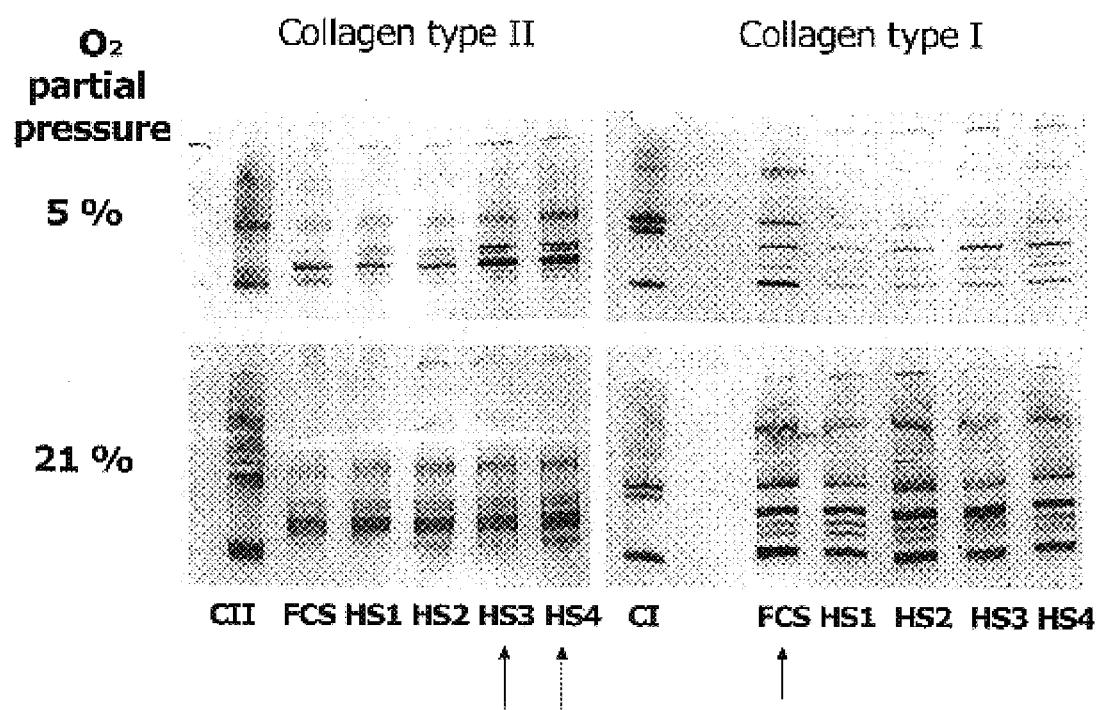

These objects are achieved by a process for the production of a human cartilage implant from chondrocytes cultivated in vitro comprising, e.g., a) subjecting cartilage (e.g., a human patient's own cartilage) to one or more extracellular matrix digesting enzymes, thereby isolating chondrocytes;

b) seeding the isolated chondrocytes in a cell culture vessel (e.g., a plate, flask or bottle) and cultivating them in a nutrient solution to which human and/or calf serum and growth factor(s) have been added;

c) subjecting the cultivated chondrocytes to an alginate phase, comprising taking up the cells in an alginate-containing buffer solution, thereby allowing encapsulation to take place, and cultivating the encapsulated cells under an oxygen partial pressure of 20% or less (e.g., 0.5 to 20%) in a nutrient solution, preferably comprising one or more chondrogenic growth factors (e.g., one or more of IGF-1, TGF-$\beta$ and IGF-II) and human serum, at about 34–39° C., for about 0.5 to 15 weeks.

d) isolating the cells from the alginate by treatment with a chelating agent (e.g., citrate, EDTA or EGTA); and e) subjecting the cells isolated from the alginate to an aggregation phase, comprising centrifuging the isolated cells from the alginate phase, thereby forming an aggregate of cells, cultivating the centrifuged cells, e.g., for a few days, in a nutrient solution comprising one or more chondrogenic growth factors and human serum, re-embedding the aggregate thus formed in an agarose-coated surface (e.g., an agarose coated well of a plate), and cultivating the aggregated cells under an oxygen partial pressure of 21%, in a nutrient solution, for example, comprising one or more chondrogenic growth factors (e.g., one or more of IGF-1, TGF-$\beta$ and IGF-II) and human serum.

The process described above can be used not only for human chondrocytes. It is likewise suitable for pig chondrocytes, as has been shown in an animal model. The method is also suitable for the production of chondrocytes from other species (for example camel, dromedary, horse, dog or cat). Autologous cells are preferably used, but the process can also employ heterologous and non-heterologous cells.

While the process is described using chondrocytes, the process is also applicable to mesenchymal stem cells. Other suitable cells include embryonic stem cells, and cells which can de-differentiate and then re-differentiate, such as, e.g., osteoblasts, adipocytes, and cells from tissues such as bone marrow, bone, cartilage, connective tissue and fat tissue.

As already mentioned above, the process according to the invention utilizes the conventional process of including chondrocytes in an alginate gel in order to re-differentiate them. Important for success in this alginate phase, however, are the modified culture conditions used in the inventive process: use of a human serum (instead of a fetal calf serum), at about 1 to 20%, preferably about 1 to 6%, by vol. of medium addition; the addition of one or more chondrogenic growth factors (e.g., IGF-I, TGF-$\beta$ and/or TGF II, preferably IGF-1 and TGF-$\beta$,); and/or the reduction in the oxygen partial pressure to less than 20%, preferably below 10%, particularly below 5% by volume (e.g., 0.5 to 20%, preferably about 1 to 15%, by volume). Using these conditions, applied over about 0.5 to 15 weeks, preferably about 1 to 6 weeks, one can obtain chondrocytes which can subsequently be aggregated for the actual cartilage formation. IGF-II can be used instead of IGF-I. The addition of one or more cytokines, e.g., interleukin 4 (IL-4), additionally stimulates cartilage formation. In a preferred embodiment, all three of the modified culture conditions discussed above are used in this alginate culture step.

In the case of chondrocytes expanded in vitro, the inclusion in alginate gel has hitherto been described as a method which is suitable for demonstrating the basic chondrogenesis potential (Yaeger P. C. et al. Exp. Cell Res. 237:318–325 (1997) Synergistic Action of Transforming Growth Factor-β and Insulin-like Growth Factor-I Induces Expression of Type II Collagen and Aggrecan Genes in Adult Human Articular Chondrocytes). However, if, e.g., human serum and/or a reduction in oxygen partial pressure are not used during the incubation of the alginate cultures, the resultant cells are poorly suitable for the preparative production of human cartilage tissue. In such a process, the chondrone-like structures (referred to below as "chondrones"), obtained by careful dissolution of the alginate gel by chelating agents, such as citrate, EDTA or EGTA, have a high collagen type I content and do not exhibit the tendency to form cartilage tissue on aggregation.

The importance of a minimal content of collagen type I in chondrones has also been demonstrated in an animal model. Pig chondrocytes were expanded in vitro and cultivated in alginate gel for 8–12 days under normal (21%) oxygen partial pressure, in the presence of chondrogenic growth factors. Only following this procedure chondrones obtained from the gel, had a minimal content of collagen type I and were able to subsequently form hyaline cartilage. Only pig chondrones having such a low collagen type I content were able to form hyaline cartilage having the desired high ratio of collagen type II/collagen type I. By contrast, re-differentiation of human chondrones requires cultivation under the above-mentioned conditions for several weeks, preferably about 1 to 6 weeks.

Preference is furthermore given to a process as above, further comprising centrifuging the isolated chondrocytes from the alginate phase onto a flat surface to form cartilage having a sheet-like shape. The chondrocytes are centrifuged in a centrifuge tube having a flat base. Sheet-like cartilage aggregates as preferred for implantation tend to form in this case. In addition, the sheet-like shape of the implants offers an advantage for supply/disposal during in vitro cultivation owing to the short diffusion distances.

Preference is furthermore given to a process as described above, in which the chondrogenic growth factors are IGF-1 and TGF-β, preferably in the ratio 5–10: 1 (w:w). The addition of interleukin 4, preferably at about 0.1–3 ng/ml, for further promotion of chondrogenesis is likewise preferred.

Preference is furthermore given to a process as described above, in which the oxygen partial pressure is reduced to less than 10%. A reduced partial pressure of 5% is particularly preferred. The importance of the effect of a reduced oxygen partial pressure on the ratio between collagen type I and type II for differentiation of human chondrocytes can be seen from FIG. 1.

Preference is also given to a process in which up to 20% by vol. of human serum are used as medium addition for the preparation of the aggregate culture. A medium addition of 10% by vol. of human serum is particularly preferred. Also, during the aggregate phase, chondrogenic growth factors (e.g., IGF-I, TGF-β and/or IGF-II) can be present in the nutrient growth medium.

Preference is also given to a process in which chondrocytes are kept in monolayer culture for up to 12 passages, preferably for no more than 7 passages.

In the aggregate phase, the oxygen partial pressures are preferably 21% by volume, although other pressures can be used, e.g., 2 to 21%, preferably 5 to 21% by volume.

Preference is furthermore given to a process in which a high collagen type II/type I ratio results. A high collagen type II/type I ratio is an indication that collagen type I preferably occurs in the thin outer layer, as desired. Precise quantitative data can be derived from immunological analyses, but are dependent on the absolute size of the samples. In the prior art, the surface layer accounts for only 10–20% of the total content of the cartilage formed, and this layer is primarily collagen type I (T. Minas & S. Nehrer Orthopedics 20 (6): 525–538 (1997) Current concepts in treatment of articular cartilage defects).

The abbreviations given above and below have the following meanings:

| | |
|---|---|
| PBS | phosphate-buffered saline solution |
| DMEM | Dulbecco's modified eagle medium, high glucose |
| DMEM/Ham's F12 | . . . nutrient mix F12 (1:1) |
| bFGF | basic fibroblast growth factor |
| EGF | epidermal growth factor |
| FCS | fetal calf serum |
| HEPES | N-2-hydroxyethylpiperazine-N'-2-ethanesulfonic acid |
| IGF or IGF-I | insulin-like growth factor 1 |
| TGF-β | transforming growth factor β |
| IL-4 | interleukin 4 |
| w:w | weight by weight |

The invention is described explained in greater detail below with reference to two working examples.

In the foregoing and in the following examples, all temperatures are set forth uncorrected in degrees Celsius; and, unless otherwise indicated, all parts and percentages are by weight.

EXAMPLES

Working Example 1

Isolation of Chondrocytes

Joint cartilage from the head of the radius of a 60-year-old female patient was peeled off, freed from all blood and tissue residues and cut up using a scalpel in a Petri dish. The cartilage pieces were placed on the sieve of a digestion chamber with magnetic stirrer and stirred at 37° C. for 25 minutes with 50 ml of hyaluronidase solution (25 mg of hyaluronidase in 50 ml of PBS). The tissue was then incubated with 50 ml of 0.25% by weight trypsin/EDTA (45 min., 37° C., stirred) and washed for 5 minutes with 50 ml of DMEM+10% by vol. of FCS. The dissolution of the chondrocytes out of the tissue structure was carried out with a three-fold collagenase treatment (collagenase 1a), in which the tissue was incubated at 37° C. with stirring with 50 ml of collagenase solution (25 mg in 50 ml of DMEM+10% by vol. of FCS+100 U/ml of penicillin+100 µg/ml of streptomycin), and the cells were centrifuged off (500×g, 5 min) from the solution which had dripped through. The tissue was digested with collagenase firstly for 2 hours and later twice overnight. Further cells were subsequently rinsed out of the tissue and centrifuged off as before through addition of DMEM+10% by vol. of FCS.

Monolayer Cultivation

The isolated chondrocytes were seeded at a density of $10^4$ cells/cm² in cell culture bottles and cultivated with DMEM/Ham's F12 (1/1)+10% by vol. of FCS+10 ng/ml of bFGF+1 ng/ml of EGF. The medium was changed twice per week, with the cells being passaged once per week with 0.25% by weight trypsin/EDTA. The chondrocytes were kept in the monolayer culture until the 7th passage.

Alginate Culture

After a washing step in NH buffer (0.15 M NaCl+25 mM HEPES, pH 7.4), the cells were taken up in NH buffer+1.2% by weight of potassium alginate (density 1 million cells/ml). In each case 1 ml of the cell suspension was introduced dropwise into a well of a 12-well plate (filled with 3 ml of 0.1 M $CaCl_2$/25 mM HEPES). The encapsulation of the cells in alginate was carried out immediately. The alginate beads were washed twice in NH buffer after 15 minutes.

The alginate-encapsulated cells were subsequently taken up in DMEM+10% by vol. of human serum+50 μg/ml of ascorbic acid+100 ng/ml of IGF+10 ng/ml of TGF-β and cultivated for 3 weeks at 37° C., 5% $CO_2$, 95% relative atmospheric humidity, in an incubator with the medium being changed 3 times per week. Various human sera and also FCS were tested. $O_2$ partial pressures of 5% and 21% were compared to one another (see FIG. 1).

In order to isolate the cells from the alginate, they were firstly washed twice with NH buffer before the alginate was dissolved out by addition of NH buffer+55 mM sodium citrate with tumbling for 15 minutes.

Aggregate Culture

The isolated cells were re-washed with NH buffer and centrifuged on the base, cast-out with synthetic resin, of a 15 ml Greiner tube (50×g, 10 min). After cultivation for 2 days with DMEM+10% by vol. of human serum+50 μg/ml of ascorbic acid+100 ng/ml of IGF+10 ng/ml of TGF-β, the aggregate was re-embedded in an agarose-coated well of a 12-well plate. The aggregated cells were cultivated in DMEM+10% by vol. of human serum+100 ng/ml of IGF+10 ng/ml of TGF-β+penicillin/streptomycin for 2–3 weeks under the same conditions as in the alginate culture, but at an $O_2$ partial pressure of 21%.

The process was successful with various human sera, but not with FCS.

Working Example 2

The isolation of the chondrocytes and the monolayer cultivation were carried out as described in Example 1.

The preparation of the alginate and aggregate cultures were also carried out as described in Example 1. For further stimulation of chondrogenesis, however, 2 ng/ml of the cytokine IL-4 were added during the alginate and aggregate culture.

Description of FIG. 1

HS1-HS4=various human sera
CII=collagen II (control)
CI=collagen I (control)

The bands are thicker at 21% of $O_2$ than at 5% of $O_2$. However, more collagen type I is also formed at 21% of $O_2$→the collagen type II/type I quotient is unfavourable.

At 5% of $O_2$, only a little collagen type I is formed on use of human serum. If, by contrast, FCS is used, the collagen type II/type I ratio is significantly impaired.

From the foregoing description, one skilled in the art can easily ascertain the essential characteristics of this invention and, without departing from the spirit and scope thereof, can make various changes and modifications of the invention to adapt it to various usages and conditions.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure[s] of all applications, patents and publications, cited above, and of corresponding priority document No. DE 10042484.8, filed Aug. 29, 2001 are hereby incorporated by reference.

We claim:

1. A method for the production of chondrocyte cells for aggregation, comprising subjecting in vitro cultivated chondrocytes to an alginate phase, comprising: mixing the chondrocytes in an alginate-containing buffer solution, encapsulating the chondrocytes in alginate beads, and cultivating the encapsulated chondrocytes in a nutrient solution comprising one or more chondrogenic growth factors and human serum under an oxygen partial pressure of less than 20 volume %.

2. The method according to claim 1, wherein said oxygen partial pressure is less than 10 volume %.

3. A method for the production of a cartilage implant, comprising:

a) subjecting in vitro cultivated chondrocytes to an alginate phase, comprising: mixing the chondrocytes in an alginate-containing buffer solution, encapsulating the chondrocytes in alginate beads, and cultivating the encapsulated chondrocytes in a nutrient solution under an oxygen partial pressure of less than 20 volume %; and b) subjecting the chondrocytes from the alginate phase to an aggregation phase, comprising centrifuging chondrocytes, which have been isolated from the alginate by treatment with a chelating agent, thereby forming an aggregate of cells, and cultivating the aggregate of cells under an oxygen partial pressure of 2–21 volume %, in a nutrient solution.

4. The method of claim 3, wherein the nutrient solution in the alginate phase, the aggregation phase, or both, further comprises human serum, one or more chondrogenic growth factors, or both.

5. The method of claim 3, wherein the nutrient solution in the alginate phase further comprises human serum, one or more chondrogenic growth factors, or both.

6. The method of claim 4, wherein the chondrogenic growth factors present in the alginate phase, the aggregate phase, or both, are IGF-1 and TGF-β, in a ratio of 5:10 (w:w).

7. The method of claim 4, wherein the nutrient solution in the alginate phase, in the aggregate phase, or both, further comprises at least one cytokine.

8. The method of claim 7, wherein the cytokine is interleukin-4, at a concentration of 0.1 to 3 ng/ml.

9. The method of claim 5, wherein chondrocytes are centrifuged onto a flat surface whereby the cells form a sheet-like shape.

10. The method of claim 5, wherein the oxygen partial pressure in the alginate phase is less than 10%.

11. The method of claim 5, wherein, during the alginate phase, chondrones are formed which have a high ratio of collagen type II to collagen type I.

12. The method of claim 5, wherein, during the aggregation phase, the nutrient solution comprises up to 20% by volume of human serum.

13. The method of claim 5, wherein the chondrocytes are human.

14. The method of claim 13, wherein the chondrocytes are taken from a patient into whom the cartilage implant is to be introduced.

15. The method of claim 5, further comprising, before the alginate phase, seeding chondrocytes in a cell culture vessel and cultivating them to form a monolayer in a nutrient solution to which human serum and growth factors have been added.

16. The method of claim 15, wherein the nutrient solution in which cells are cultivated to form a monolayer further comprises at least one cytokine.

17. The method of claim 16, wherein said at least one cytokine is interleukin-4 at a concentration of 0.1 to 3 ng/ml.

18. The method of claim 15, wherein the cells are kept in monolayer culture for no more than 12 passages.

19. The method of claim 15, wherein the cells are kept in monolayer culture for no more than 7 passages.

20. The method of claim 13, wherein the chondrocytes are taken from a source which is heterologous to the patient into whom the cartilage implant is to be introduced.

21. A cartilage implant obtained by the method of claim 4.

22. A method for the production of a cartilage implant, comprising:

subjecting chondrocytes from an alginate culture to an aggregation phase, comprising centrifuging chondrocytes, which have been isolated from the alginate by treatment with a chelating agent, thereby forming an aggregate of cells, and cultivating the aggregate of cells under an oxygen partial pressure of 2–21 volume %, in a nutrient solution comprising one or more chondrogenic growth factors and human serum, wherein the chondrocytes from the alginate culture have been obtained by mixing the chondrocytes in an alginate-containing buffer solution, encapsulating the chondrocytes in alginate beads, and cultivating the encapsulated chondrocytes in a nutrient solution under an oxygen partial pressure of 0.5 to 20%.

23. A method for the production of a human cartilage implant, comprising:

a) subjecting cartilage from a human patient to one or more extracellular matrix digesting enzymes, thereby isolating chondrocytes;

b) seeding the isolated chondrocytes in a cell culture vessel and cultivating said chondrocytes in a nutrient solution to which human serum and growth factors have been added;

c) subjecting the cultivated chondrocytes to an alginate phase, comprising mixing the cells in an alginate-containing buffer solution, encapsulating the chondrocytes in alginate beads, and cultivating the encapsulated cells under an oxygen partial pressure of 0.5 to 20%, at 34–39° C., for 0.5 to 15 weeks, in a nutrient solution comprising one or more chondrogenic growth factors and human serum;

d) isolating the cells from the alginate by treatment with a chelating agent; and e) subjecting the cells isolated from the alginate to an aggregation phase, comprising centrifuging the isolated cells from the alginate phase onto a flat surface, thereby forming an aggregate of cells, cultivating the centrifuged cells in a nutrient solution comprising one or more chondrogenic growth factors and human serum, re-embedding the aggregate thus formed in an agarose-coated surface, and cultivating the aggregated cells under an oxygen partial pressure of 2–21 volume % in a nutrient solution comprising one or more chondrogenic growth factors and human serum.

24. A method for the production of a cartilage implant, comprising:

a) subjecting in vitro cultivated stem cells to an alginate phase, comprising mixing the cells in an alginate-containing buffer solution, encapsulating the chondrocytes in alginate beads, and cultivating the encapsulated under an oxygen partial pressure of 0.5 to 20%, in a nutrient solution comprising one or more chondrogenic growth factors and human serum; and b) subjecting the encapsulated cells from the alginate phase to an aggregation phase, comprising centrifuging the encapsulated cells from the alginate phase onto a flat surface, thereby forming an aggregate of cells, and cultivating the aggregated cells under an oxygen partial pressure of 2–21 volume % in a nutrient solution comprising one or more chondrogenic growth factors and human serum.

* * * * *